(12) United States Patent
Sinha

(10) Patent No.: US 10,415,031 B2
(45) Date of Patent: Sep. 17, 2019

(54) METHOD, APPARATUS AND KIT FOR HUMAN IDENTIFICATION USING POLYMER FILTER MEANS FOR SEPARATION OF SPERM CELLS FROM BIOLOGICAL SAMPLES THAT INCLUDE OTHER CELL TYPES

(71) Applicant: InnoGenomics Technologies, LLC, New Orleans, LA (US)

(72) Inventor: Sudhir Sinha, New Orleans, LA (US)

(73) Assignee: InnoGenomics Technologies, LLC, New Orleans, LA (US)

( * ) Notice: Subject to any disclaimer, the term of this patent is extended or adjusted under 35 U.S.C. 154(b) by 575 days.

(21) Appl. No.: 15/016,110

(22) Filed: Feb. 4, 2016

(65) Prior Publication Data

US 2016/0222375 A1 Aug. 4, 2016

Related U.S. Application Data

(60) Provisional application No. 62/142,308, filed on Apr. 2, 2015, provisional application No. 62/115,965, filed on Feb. 13, 2015, provisional application No. 62/111,911, filed on Feb. 4, 2015.

(51) Int. Cl.
  *C12Q 1/68* (2018.01)
  *C12N 15/10* (2006.01)
(52) U.S. Cl.
  CPC ................... *C12N 15/1017* (2013.01)
(58) Field of Classification Search
  None
  See application file for complete search history.

(56) References Cited

U.S. PATENT DOCUMENTS

| | | |
|---|---|---|
| 5,575,914 A | 11/1996 | Jeyendran |
| 5,976,389 A | 11/1999 | Zavos |
| 6,129,214 A | 10/2000 | Bar-Ami et al. |
| 7,320,891 B2 | 1/2008 | Tereba et al. |
| 8,703,416 B2 | 4/2014 | Sanders et al. |
| 2003/0215845 A1 | 11/2003 | Bille |
| 2006/0141512 A1 | 6/2006 | Sinha et al. |
| 2006/0230731 A1* | 10/2006 | Kalayci .............. B01D 39/1623 55/486 |
| 2008/0176320 A1 | 7/2008 | Liu |
| 2009/0042255 A1 | 2/2009 | Liu |
| 2010/0099075 A1 | 4/2010 | Ferraz Pedrazzi |
| 2011/0223653 A1 | 9/2011 | Chakrabarty |

FOREIGN PATENT DOCUMENTS

| WO | 2008/089280 | 7/2008 |
|---|---|---|
| WO | 2012/174496 | 12/2012 |

OTHER PUBLICATIONS

Garvin, Filtration Based DNA Preparation for Sexual Assault Cases, J. Forensic Sci. 48(5), 1-4 (2003). (Year: 2003).*
Weedn and Hicks, The unrealized potential of DNA testing, National Institute of Justice Journal, Issue 234, (Dec. 16-23, 1997).
Budowle et al., Simple protocols for typing forensic biological evidence: chemiluminescent detection for human DNA quantitation and restriction fragment length polymorphism (RFLP) analyses and manual typing of polymerase chain reaction (PCR) amplified polymorphisms, Electrophoresis, 16(9): 1559-1567 (1995).
Oda et al., Infrared-mediated thermocycling for ultrafast polymerase chain reaction amplification of DNA, Anal. Chem., 70(20): 4361-4368 (1998).
Hühmer and Landers, Noncontact infrared-mediated thermocycling for effective polymerase chain reaction amplification of DNA in nanoliter volumes, Anal. Chem., 72(21): 5507-5512 (2000).
Giordano et al., Polymerase chain reaction in polymeric microchips: DNA amplification in less than 240 seconds, Anal. Biochem., 291(1): 124-132 (2001).
Lagally et al., Single-molecule DNA amplification and analysis in an integrated microfluidic device, Anal. Chem., 73(3): 565-570 (2001).
Lagally et al., Fully integrated PCR-capillary electrophoresis microsystem for DNA analysis, Lab on a Chip, 1(2): 102-107 (2001).
Schmalzing et al., DNA typing in thirty seconds with a microfabricated device, Proc. Natl. Acad. Sci., 94(19): 10273-10278 (1997).
Emrich et al., Microfabricated 384-lane capillary array electrophoresis bioanalyzer for ultrahigh-throughput genetic analysis, Anal. Chem., 74(19): 5076-5083 (2002).
Perlin et al., Validating TrueAllele® DNA mixture interpretation, J. Forensic Sci., 56(6): 1430-1447 (2011).
Brinkerhoff and Straehley, FBI Errors Lead to Discovery that DNA Evidence May be Far Less Foolproof When It Includes More than One Person, published online on Sep. 10, 2015, 2 pages, http://www.allgov.com/news/unusual-news/fbi-errors-lead-to-discovery-that-dna-evidence-may-be-far-less-foolproof-when-it-includes-more-than-one-person-150910?news=857388.
Wiegand et al., DNA extraction from mixtures of body fluid using mild preferential lysis, Int. J. Legal Med., 104, 359-360 (1992).
Gill et al., Forensic application of DNA 'fingerprints', Nature, 318(6046): 577-579 (1985).

(Continued)

*Primary Examiner* — Kenneth R Horlick
(74) *Attorney, Agent, or Firm* — Robert E. Bushnell, Esq.

(57) ABSTRACT

A method for processing forensic samples that include sperm cells from a perpetrator of sexual assault and epithelial cells that are primarily contributed by the victim is provided. The method includes providing a nanofiber filter that is formed of intermingled nanofibers having diameters of about 700 nm or less, selectively digesting the epithelial cells of a forensic sample and separating the sperm cells of the sample from the digested epithelial cells by filtration of the digest mixture through the nanofiber filter, the sperm cells becoming entrapped in the nanofiber filter. The captured sperm cells may then be digested to form a second digest mixture including digested sperm cell DNA. Using the first digest mixture filtrate and the second digest mixture, respectively, DNA samples may be isolated and DNA profiles may be obtained, the DNA profiles being useful for human identification. An apparatus and a kit for processing forensic samples obtained in sexual assault cases are also provided.

33 Claims, 5 Drawing Sheets

(56) References Cited

OTHER PUBLICATIONS

Qiagen Supplementary Protocol: Purification of DNA from epithelial cells mixed with sperm cells using the MagAttract® DNA Mini M48 Kit, Qiagen, 4 pages (2010).
Yoshida et al., The modified method of two-step differential extraction of sperm and vaginal epithelial cell DNA from vaginal fluid mixed with semen, Forensic Sci. Int., 72(1): 25-33 (1995).
Eisenberg, Development of a spermatozoa capture system for the differential extraction of sexual assault evidence, presented at Profiling PCR and Beyond, Washington, DC, Jun. 28, 2002.
Elliott et al., Use of laser microdissection greatly improves the recovery of DNA from sperm on microscope slides, Forensic Sci. Int, 137(1): 28-36 (2003).
Schoell et al., Separation of sperm and vaginal cells with flow cytometry for DNA typing after sexual assault, Obstet. Gynecol., 94(4): 623-627 (1999).
Li et al., Magnetic bead-based separation of sperm from buccal epithelial cells using a monoclonal antibody against MOSPD3, Int. J. Legal Med., 128(6): 905-911 (2014).
Horsman et al., Separation of sperm and epithelial cells in a microfabricated device: potential application to forensic analysis of sexual assault evidence, Anal. Chem., 77(3): 742-749 (2005).
Garvin et al., DNA preparation from sexual assault cases by selective degradation of contaminating DNA from the victim, J. Forensic Sci., 54(6): 1297-1303 (2009).
Garvin et al., Isolating DNA from sexual assault cases: a comparison of standard methods with a nuclease-based approach, Investigative Genetics, 3: 25, 10 pages (2012).
Chen et al., A physical method for separating spermatozoa from epithelial cells in sexual assault evidence, J. Forensic Sci., 43(1): 114-118 (1998).
Huang et al., A review on polymer nanofibers by electrospinning and their applications in nanocomposites, Composites Science and Technology, 63, 2223-2253 (2003).
Taghavi and Larson, Regularized thin-fiber model for nanofiber formation by centrifugal spinning, Phys. Rev., E 89, 023011, 1-9 (2014).
Roush and Lu, Advances in primary recovery: centrifugation and membrane technology, Biotechnology Progress, 24 (3): 488-495 (2008).
Van Reis and Zydney, Membrane separations in biotechnology, Current Opinion in Biotechnology, 12(2): 208-211 (2001).
Barhate et al., Preparation and characterization of nanofibrous filtering media, J. Membrane Sci., 283(1-2): 209-218 (2006).
Li and Xia, Direct fabrication of composite and ceramic hollow nanofibers by electrospinning, Nano Letters, 4(5): 933-938 (2004).
Grimes, Synthesis and application of highly ordered arrays of $TiO_2$ nanotubes, J. Materials Chem., 17(15): 1451-1457 (2007).
Bellastella et al., Dimensions of human ejaculated spermatozoa in Papanicolaou-stained seminal and swim-up smears obtained from the Integrated Semen Analysis System (ISAS®), Asian Journal of Andrology, 12(6): 871-879 (2010).
Gautam et al., Electrospun polyimide nanofiber membranes for high flux and low fouling microfiltration applications, Journal of Membrane Science, 466, 142-150 (2014).
Zhang et al., Fabrication and bioseparation studies of adsorptive membranes/felts made from electrospun cellulose acetate nanofibers, Journal of Membrane Science, 319, 176-184 (2008).
Schneiderman et al., Surface-functionalized electrospun carbon nanofiber mats as an innovative type of protein adsorption/purification medium with high capacity and high throughput, Journal of Chromatography A, 1218, 8989-8995 (2011).
Zhang and Lu, Centrifugal Spinning: An Alternative Approach to Fabricate Nanofibers at High Speed and Low Cost, Polymer Reviews, 54(4): 677-701 (2014).

\* cited by examiner

METHOD, APPARATUS AND KIT FOR HUMAN IDENTIFICATION USING POLYMER FILTER MEANS FOR SEPARATION OF SPERM CELLS FROM BIOLOGICAL SAMPLES THAT INCLUDE OTHER CELL TYPES

CLAIM OF PRIORITY

This application makes reference to, incorporates the same herein, and claims all benefits accruing under 35 U.S.C. § 119 from an application for METHOD, APPARATUS AND KIT FOR HUMAN IDENTIFICATION USING POLYMER FILTER MEANS FOR SEPARATION OF SPERM CELLS FROM BIOLOGICAL SAMPLES THAT INCLUDE OTHER CELL TYPES, earlier filed in the United State Patent and Trademark Office on 2 Apr. 2015 and there duly assigned Ser. No. 62/142,308, from an application for METHOD, APPARATUS AND KIT FOR SEPARATION OF SPERM CELLS, SPERM CELL DNA AND OTHER DNA FROM FORENSIC SAMPLES earlier filed in the United State Patent and Trademark Office on 13 Feb. 2015 and there duly assigned Ser. No. 62/115,965, and from an application for METHOD FOR SEPARATION OF SPERM CELLS FROM OTHER CELL TYPES IN BIOLOGICAL SAMPLES USING NANOFIBER MATERIALS FOR HUMAN IDENTIFICATION APPLICATIONS earlier filed in the United State Patent and Trademark Office on 4 Feb. 2015 and there duly assigned Ser. No. 62/111,911.

BACKGROUND OF THE INVENTION

1. Field of the Invention

The present application describes methods for separating sperm cells, sperm cell DNA, and other DNA from biological samples comprising both sperm cells and epithelial cells. The methods include selective digestion of epithelial cells and subsequent removal of sperm cells from the mixture by filtration through a nanofiber filter. DNA profiles obtained from the separated components of forensic samples are suitable for use in human identification.

2. Description of the Related Art

Forensic DNA testing has become widely used in sexual assault cases. However, because of the increasing use of DNA analysis and the lack of sufficient funding, a major backlog of cases waiting to be analyzed currently exists throughout the United States. The backlog of untested evidence in sexual assault cases is an important, controversial challenge facing our nation today. It is not uncommon for sexual assault kit (or "rape kit") evidence to be stored for years before analysis, if analyzed at all. The backlog of rape kit evidence was estimated at 400,000 cases nationwide in 2014 (cnn.com, accessed Dec. 11, 2014: "400,000 rape kits left untested in U.S.").

The reasons that large numbers of sexual assault kits are stored untested in police property rooms around the country are complex. Based on various circumstances, investigators or prosecutors may not have submitted them to a laboratory and requested that they be analyzed. Law enforcement agencies often lack the technology to track untested rape kits and the personnel needed for shipping or transporting untested kits to a crime lab in a timely manner. These agencies further lack resources and staffing to investigate and follow up on leads resulting from rape kit testing. Once in the forensic science laboratory, laboratory directors fault the time and cost requirements of these analyses as the bottleneck to DNA analysis (V. W. Weedn & J. W. Hicks, *The unrealized potential of DNA testing*, National Institute of Justice Journal, Issue 234 (December, 1997)). The most time-consuming step in DNA analysis of sexual assault evidence is the conventional differential extraction process that is used to separate sperm cells from other types of cells in a sexual assault sample (B. Budowle, et al., *Simple protocols for typing forensic biological evidence: chemiluminescent detection for human DNA quantitation and restriction fragment length polymorphism (RFLP) analyses and manual typing of polymerase chain reaction (PCR) amplified polymorphisms*, Electrophoresis 16(9): 1559-1567 (1995)). Therefore, the development of a quick, accurate, and effective method to streamline the differential extraction process would be advantageous in reducing, the rape kit backlog that exists in crime laboratories across the country today.

Forensic DNA analysis of sexual assault samples first requires extraction of the DNA in a differential manner to obtain separate male and female fractions of DNA from the sperm and epithelial cell donors, respectively. The female fraction can be used to verify the presence of the victim's DNA, and the male fraction to identify the perpetrator, or sperm donor. DNA extraction is typically followed by real-time polymerase chain reaction (PCR) quantitation, PCR amplification of genetic markers, separation of the PCR products, and data analysis. To date, efforts have been directed toward improving the speed and efficiency of sample processing for the latter steps, namely PCR (R. P. Oda, et al., *Infrared-mediated thermocycling for ultrafirst polymerase chain reaction amplification of DNA*, Anal. Chem. 70(20): 4361-4368 (1998); A. F. R. Huhmer & J. P. Landers, *Noncontact infrared-mediated thermocycling for effective polymerase chain reaction amplification of DNA in nanoliter volumes*, Anal. Chem. 72(21); 5507-5512 (2000); B. C. Giordano, et al., *Polymerase chain reaction in polymeric microchips: DNA amplification in less than 240 seconds*, Anal. Biochem. 291(1): 124-132 (2001); E. T. Lagally, et al., *Single-molecule DNA amplification and analysis in an integrated microfluidic device*, Anal. Chem. 73(3): 565-5µ(2001); E. T. Lagally, et al., *Fully integrated PCR-capillary electrophoresis microsystem for DNA analysis*, Lab on a Chip 1(2): 102-107 (2001)), DNA separation (D. Schmalzing, et al., *DNA typing in thirty seconds with a microfabricated device*, Proc. Nat. Acad. Sci. 94(19): 10273-10278 (1997); C. A. Emrich, et al., *Microfabricated 384-lane capillary array electrophoresis bioanalyzer for ultra-high-throughput genetic analysis*, Anal. Chem. 74(19): 5076-5083 (2002)), and data analysis (M. W. Perlin, et al., *Validating TrueAllele® DNA mixture interpretation*, J. Forensic Sci. 56(6): 1430-1447 (2011)). The ability to reproducibly obtain clean sperm fraction DNA profiles from the differential extraction impacts the downstream processes, namely the time required for data analysis and interpretation is drastically less for a profile containing one donor versus one containing a mixture of donors. Sperm profiles containing a mixture of victim and perpetrator DNA oftentimes lead to difficult result interpretation, and this is currently a controversial topic in the forensic field (Brinkerhoff and Straehley, *FBI Errors Lead to Discovery that DNA Evidence May be Far Less Foolproof When It includes More than One Person*, http://www.allgov.com/news/unusual-news./fbi-errors-lead-to-discovery-that-dna-evidence-may-be-far-less-foolproof-when-it-includes-more-than-one-person-150910?news=857388) (accessed 2 Feb. 2016). However, little improvement has been made in the differential extraction process, which is the most important and most time-consuming step of the DNA analysis. In particular, robotic automation of the extensive differential extraction process has been shown to improve sample processing efficiency and throughput (12).

Sperm cell donor DNA is typically most easily obtained from sperm cells collected on vaginal swabs, taken in the routine collection of sexual assault evidence. The majority of genetic material collected on such swabs is from the victim (P. Wiegand, et al., *DNA extraction from mixtures of body fluid using mild preferential lysis*, Int. J. Legal Med. 104: 359-360 (1992)), mainly from epithelial cells that are collected from the vaginal lining. These cells, or DNA from these cells, must be separated from the sperm cells before sperm DNA is recovered and amplified for analysis by capillary electrophoresis. The standard process to isolate sperm cells from the victim's cells in forensic samples is performed in most crime laboratories by chemical means, involving differential lysis of the cells collected on the vaginal swab and exploiting the differential stability of the cell membranes reported in 1985 by P. Gill and coworkers (P. Gill, et al., *Forensic application of DNA 'fingerprints'*, Nature 318(6046): 577-579 (1985); Qiagen Supplementary Protocol: Purification of DNA from epithelial cells mixed with sperm cells using the MagAttract® DNA Mini M48 kit. Qiagen (2010); K. Yoshida, et al., *The modified method of two-step differential extraction of sperm and vaginal epithelial cell DNA from vaginal fluid mixed with semen*, Forensic Sci. Int. 72(1): 25-33 (1995)). This multistep procedure begins by lysing the epithelial cells using mild conditions. The intact sperm cells (predominately heads because tails are often degraded) are pelleted by centrifugation, allowing the soluble DNA from the epithelial cells to be removed in the supernatant (this becomes known as the "epithelial" or "non-sperm" fraction). Several washing and centrifugation steps are involved in this process to remove non-sperm DNA from the sperm cells during which the analyst attempts to pipette as much of the supernatant (epithelial cell fraction) as possible from the tube with the sperm pellet without disturbing the sperm pellet. The several centrifugation and washing steps typically result in significant loss of valuable sperm cell evidence. The pelleted sperm cells are then suspended and lysed using a proteinase enzyme such as proteinase K in a buffer that contains detergent and a reducing agent such as dithiothreitol (DTT) for reduction of disulfide bonds. The DNA is extracted using phenol/chloroform/isoamyl alcohol or other DNA isolation methods. This process of partial digestion is commonly referred as the differential digest procedure. This differential extraction procedure is time consuming, not amenable to automation, and prone to loss of valuable crime scene evidence (Budowle, et al., cited above).

When the amount of epithelial cell DNA is very large and there are relatively few sperm cells, it is often difficult and sometimes impossible to remove enough of the epithelial DNA so that a clean sperm DNA profile is obtained, and the result oftentimes is a mixed DNA profile. Although this is the most common differential extraction method used by crime laboratories, it is very technique-dependent, and the quality of results can vary between analysts or technicians. The sperm pellet washing steps can be inefficient at removing soluble DNA from the cell pellet, leading to incomplete separation of sperm and non-sperm fractions, particularly in samples that contain large numbers of the victim's cells relative to sperm cells. In addition, the time-consuming nature of the process precludes this method as a viable solution in an efficiency-minded laboratory.

Over the last 30 years, several attempts have been made to address the inherent complexity and drawbacks of this method, attempting to improve ease of use, ability to automate and yield of recovered sperm DNA from forensic samples, particularly sexual assault kits. Following are the different approaches previously proposed to replace the centrifugation based differential digest protocol:

Density Medium Based Separation:

The separation is done by contacting the aqueous sample with a non-aqueous liquid having a density greater than about 1.00 g/cm$^3$, wherein the density of the non-aqueous liquid is sufficiently low to permit pelleting of at least a portion of the sperm cells in the sample. A commercial kit is available from Promega Corporation (A. Tereba, et al., *Methods and kits for isolating sperm cells*, U.S. Pat. No. 7,320,891 B2, issued Jan. 22, 2008) and is in use in some laboratories. However, the process is still not easy to perform and sperm DNA separation/recovery can be variable and sub-optimal. Although it can be automated, this is much more complex than the manual method.

Immunological or Other Affinity Based Methods:

A reasonable alternative to the current method involves the separation of the sperm and epithelial cells before DNA extraction. Eisenberg (A. J. Eisenberg, *Development of a spermatozoa capture system for the differential extraction of sexual assault evidence*, presented at Profiling PCR and Beyond, Washington, D.C., Jun. 28, 2002) has addressed the separation of sperm and epithelial cells through the development of antibody-based separation schemes, using magnetic beads with covalently bound sperm-specific antibodies to selectively retain the sperm heads. There are potential problems associated with this approach, most notably clogging of the separation column by the large numbers of epithelial cells in casework samples. In addition to clogging, drawbacks of this technique include the cost of the materials required for the antibody/bead separation method, combined with the numerous steps requited to yield PCR-ready DNA.

A second method for the selection of sperm cells was reported by Elliott and coworkers (K. Elliott, et al., *Use of laser microdissection greatly improves the recovery of DNA from sperm on microscope slides*, Forensic Sci. Int. 137(1); 28-36 (2003)), who prepared slides from swabs and then selectively captured the sperm cells from the slide, using laser capture micro dissection. This method is also capable of isolating the sperm cells selectively; however, it is time-consuming, labor-intensive (to identify the sperm cells in the sample), and not likely to be amenable to high-throughput applications. In a similar process, Schoen and coworkers (W. M. Schoell, et al., *Separation of sperm and vaginal cells with flow cytometry for DNA typing after sexual assault*, Obstet. Gynecol. 94(4): (23-627 (1999)) demonstrated a fluorescence-activated cell sorting method for the separation of sperm and vaginal cells. However, the authors indicate that the use of this method would require altering the collection of evidentiary samples from vaginal swabs to vaginal lavages. Several other variations of the antibody based approach have been attempted and reported in the literature (G. Sanders, et al., *Method for purification and identification of sperm cells*, U.S. Pat. No. 8,703,416 B2, issued Apr. 22, 2014; Li, et al., *Magnetic bead-based separation of sperm from buccal epithelial cells using a monoclonal antibody against MOSPD3*, Int. J. Legal Med. 128: 905-911 (2014). An affinity binding approach using sperm binding protein was suggested by Sinha (S. K. Sinha, et al., *Novel method for separation of human sperm from biological samples for application in human identification*, U.S. Patent Application Pub. 2006/0141512 A1, published Jun. 29, 2006).

Microfluidic Based Methods:

The research group of Landers reported a microfluidic based platform to create an automated sperm separation apparatus (K. M. Horsman, et al., *Separation of sperm and epithelial cells in a microfabricated device: potential application to forensic analysis of sexual assault evidence*, Anal. Chem. 77(3): 742-749 (2005)). This separation utilizes the differential physical properties of the cells that result in settling of the epithelial cells to the bottom of the inlet reservoir and subsequent adherence to the glass substrate. As a result, low flow rates can be used to separate the sperm cells from the epithelial cell-containing biological mixture.

Another approach using a micro fabricated device used holographic optical trapping to sort objects and contaminants. This may be done using a chip for sorting utilizing holographic optical trapping (HOT), in the absence or presence of microfluidic streaming and sorting (T. Chakrabarty, *Method and apparatus for sorting objects in forensic DNA analysis and medical diagnostics*, U.S. Patent Application Pub. 2011/0223653 A1, published Sep. 15, 2011).

DNAse Digestion Based Method:

A promising method reported by Garvin and coworkers (A. M. Garvin, et al., *DNA preparation from sexual assault cases by selective degradation of contaminating DNA from the victim*, J. Forensic Sci. 54(6): 1297-1303 (2009)) is based on purifying sperm DNA from vaginal swabs taken from rape victims by selectively digesting the victim's epithelial cells to solubilize the victim's DNA, and to remove the soluble victim's DNA by selectively degrading it using, a nuclease, DNase I. Although the method works (A. M. Garvin, et al., *Isolating DNA from sexual assault cases: a comparison of standard methods with a nuclease-based approach*, Investigative Genetics 3: 25 (2012)), the fear of introducing a DNA degrading enzyme, in a valuable forensic DNA sample, is not appealing to forensic scientists.

Selectively Lysing the Sperm Cells:

In an approach opposite to the commonly used method whereby the non-sperm cells are lysed and intact sperm cells are recovered by centrifugation (P. Gill, et al., cited above), this method selectively lyses the sperm cells in presence of other cell types and collects the sperm DNA. The sperm cell lysis is effected by chemical reagents such as DTT in buffer (J. Y. Liu, *Method for recovering sperm nucleic acid from a forensic sample*, U.S. Patent Application Pub. No 2009/0042255 A1, published Feb. 12, 2009).

Physical Separation by Filtration Based Methods:

Chen and coworkers (J. Chen, et al., *A physical method for separating spermatozoa from epithelial cells in sexual assault evidence*, J. Forensic Sci. 43(1): 114-118 (1 998)) demonstrated a separation of sperm cells from a mixture of sperm and epithelial cells using an 8-μm nylon mesh membrane filter, which retains the larger epithelial cells but allows the sperm cells to pass through it. In this method about 70% of the smaller sperm cells will pass through the filter whereas only 1-2% of the larger epithelial cells will pass through the membrane filter. However, the presence of female DNA in the sperm cell fraction is a factor in this method, because epithelial cells easily lyse, allowing free DNA or epithelial cell nuclei to in pass through the nylon mesh filter. Following the separation in all of these techniques, the purified sperm undergo normal forensic DNA analysis for genetic identification.

Another filtration method proposed by Garvin reports separation of sperm and non-sperm cells utilizing a track-etched filter or a laser track etched filter, or a combination of the two. The track etched filter typically has a mean pore size of about 2 μm. This method is similar to the method reported by Chen (Id.), but instead of nylon filters uses a track etched filter of defined pore size (A. M. Garvin, *Filtration based DNA preparation for sexual assault cases*, J. Forensic Sci. 48(5): 1084-1087 (2003)).

Description of Polymers Useful in the Invention:

Nanofibers are often defined as fibers with diameters of less than 100 nanometers ($1\times10^{-7}$ m). However, for the present purpose, nanofibers having diameters as large as about 700 nm may be useful. Nanofibers can be produced by interfacial polymerization, electrospinning or electrostatic spinning, melt-blowing, bicomponent fiber spinning, phase separation, template synthesis, or self-assembly using a variety of materials. Nanofibers can be produced from many synthetic polymers such as vinyl polymers, acrylic polymers, polyesters, polyethers, polycarbonate and polyimides. Many other types of polymer and copolymers using several biocompatible polymers such as polycaprolactone have been reported to be used to produce nanofibers (H. Fong & D. H. Reneker, in *Structure formation in polymeric fibers: Chapter 6, Electrospinning and formation of nanofibers*, D. R. Salem, ed., Munich: Carl Hanser Verlag, pp. 225-246, 2001 (ISBN: 3-446-18203-9); T. J. Menkhaus, et al., *Applications of electrospun nanofiber membranes for bioseparations*, Hauppauge, N.Y.: Nova Science Publishers, 2010 (ISBN: 978-1608767823); Z.-M. Huang, et al., *A review on polymer nanofibers by electrospinning and their applications in nanocomposites*, Composites Science and Technology 63: 2223-2253 (2003)).

The electrospinning process provides the ability to produce nanofibers from various materials in large quantity with specific application based properties. Recently, nanofiber membranes have been used for many bio-separation applications (31). Nanofibers can be modified with specific functional groups and specific biomolecules can be covalently attached for affinity separations. Many biomolecules such as proteins, DNA, and pathogens can be captured on certain nanofibers using adsorption processes.

Another way of producing nanofibers is by centrifugal spinning, which allows production of a variety of materials at high speed and low cost (Taghavi and Larson, *Regularized thin-fiber model for nanofiber formation by centrifugal spinning*, Phys. Rev. E 89 and Zhang and Lu, *Centrifugal Spinning: An Alternative Approach to Fabricate Nanofibers at High Speed and Low Cost*, Polymer Reviews Volume 54, Issue 4, 2014). In centrifugal spinning, the spinning fluid is placed in a rotating spinning head. When the rotating speed reaches a critical value, the centrifugal force overcomes the surface tension of the spinning fluid to eject a liquid jet from the nozzle tip of the spinning head. The jet then undergoes a stretching process and is eventually deposited on the collector, forming solidified nanofibers. Centrifugal spinning is simple and enables the rapid fabrication of nanofibers for various applications. Nanofibers composed of polypropylene, polyvinylidine fluoride, or polybutylene terephthalate can be produced with this method.

Separation with Nanofiber Membranes:

Separations with nanofiber membranes can be accomplished by using nanofiber layers of selected apparent pore size as a filtration membrane. Hollow nanofiber tube bundles can also be used by aligning the flow parallel to the nanofiber tube. Size based separations are routinely used for bioprocessing. Depth filtration and microfiltration are common operations used for clarification of fermentation broth where cells of approximately 20-200 nm and cellular debris 0.1-1 μm are removed from bioreactors (D. J. Roush & Y. Lu, *Advances in primary recovery: centrifugation and membrane technology*, Biotechnology Progress 24(3): 488-49

(2008)). Nanofiltration with membranes is used for viral clearance and/or purification of 20-200 nm virus particles, and ultrafiltration is commonly used for purification or separation of proteins (R. van Reis & A. Zydney, *Membrane separations in biotechnology*, Current Opinion in Biotechnology 12(2): 208-211 (2001)). In these cases, well defined pore size and size cutoff is needed to make effective separation. Also high porosity of materials is needed to avoid fouling and subsequent clogging of the membrane. Another important characteristic required when separating biomolecules with nanofiltration is chemical and physical robustness. Nanofiber felts can be produced from mechanically and chemically strong fibers with well controlled pore size among fibers or can be produced as collections of hollow fibers. These nanofiber production features offer a unique opportunity for using them as a size based separation medium for specific bio-particles or cells such as sperm cells. Polymer, carbon and ceramic nanofibers are also able to separate with high flux (R. S. Barhate, et al., *Preparation and characterization of nanofibrous filtering media*, J. Membrane Sci. 283(1-2): 209-218 (2006)). Polymer nanofibers show in general the least amount nonspecific binding of molecules such as proteins or DNA but may suffer from less chemical robustness than the ceramic fibers. Ceramic fibers suffer from being brittle and have a potential for non-specific adsorption of bio-particles or bin-molecules resulting in fouling. However, ceramic nanofibers can withstand harsh chemical regeneration processes.

Electrospun carbon nanofibers are made from the electrospun nanofibers including polyacrylonitrile (PAN) pitch cellulose, and polyvinyl alcohol (PVA) nanofibers. Carbon nanofibers made from PAN nanofibers possess very ordered graphite crystalline structure. Pore sizes among the nanofibers can be controlled in the range from tens to hundreds of nanometers which makes the nanofiber capable of filtering contaminants with sizes larger than the apparent pore sizes of the nanofiber fabrics. This gives the nanofiber the ability to filter bacteria and viruses. Carbon nanofibers made of PVA possess a large amount of nano-sized pores (H. Fong & D. H. Reneker, cited above). Another very interesting propery of nanofiber is the ability to produce hollow nanofibers (D. Li & Y. Xia, *Direct fabrication of composite and ceramic hollow nanofibers by electrospinning*, Nano Letters 4(5): 933-938 (2004)). Such hollow nanofiber bundles can be used for size based bio-separations with liquid flowing parallel to the fiber tube (C. A. Grimes, *Synthesis and application of highly ordered arrays of $TiO_2$ nanotubes*, J. Materials Chem. 17(15): 1451-1457 (2007)).

SUMMARY OF THE INVENTION

The present invention utilizes a unique property of the nanofiber filter to overcome deficiencies that previous investigators have found to be associated with prior art methods. In a forensic sexual assault sample, the victim's epithelial cells are known to be fully chemically lysed in the presence of proteinase K and in the absence of DTT. Once lysed, the sample will contain lysed epithelial cells in the presence of perpetrator sperm cells. In a novel approach, nanofibers can be used to filter the epithelial/sperm mixture, capturing the sperm cells present in the sample on the nanofiber filter, with the lysed cellular debris going through the filter. Eluting the captured sperm cells then yields clean sperm fraction DNA fraction, which will contain only the DNA of the perpetrator's sperm cells, without any contamination from the victim's DNA or any other non-sperm DNA present in the sample. Nanofibers have several properties that allow sperm capture, including different materials, thread diameter, pore size and filter thickness. Instead of relying on a fixed pore size (which is prone to fouling and reduced yield), the nanofiber filter uses layers of nanofibers of apparent pore size small enough to trap sperm cells for effective separation of intact sperm cells from the digested non-sperm cell DNA. The method of the present invention is simple, allows for relatively clean separation of sperm cell DNA from other types of DNA in a sample, and does not necessarily require the use of sensitive antibodies, labor-intensive visual cell sorting steps, meticulous construction of microfluidic devices, or the risk of unwanted enzymatic degradation of valuable DNA evidence.

The method of the present invention is convenient for use in existing forensic laboratories and can be used with classical filter cartridges and centrifugation based methods. The method can be easily adapted to automation and high throughput processing with robotic systems having a vacuum manifold or a micro fabricated device using a flow-through nanofiber filter.

The method of the present invention makes use of nanofibers for separation of sperm cells from contaminant non-sperm cells in a forensic sample by using the nanofibers as a filtration medium.

Accordingly, one object of the present invention is to provide an efficient differential extraction process that allows for the isolation of sperm cells, sperm cell DNA and DNA from other cells present in a biological sample including both sperm cells and epithelial cells.

Another object of the present invention is to provide a DNA profiling method that allows for reliable identification of a sperm donor and an epithelial cell donor from a mixed biological sample including both sperm cells and epithelial cells.

Another object of the present invention is to provide examples of materials and dimensions of nanofiber filters that effectively allow the isolation of sperm cells from a mixed biological sample including both sperm cells and epithelial cells.

Another object of the present invention is to teach formats and structures that are appropriate for an apparatus for processing a forensic sample that includes sperm cells and not sperm cells.

Another object of the present invention is to provide a kit for more efficient processing of forensic samples obtained using sexual assault kits.

The present invention may include providing a method for processing forensic samples, the method comprising providing a nanofiber filter, the nanofiber filter comprising intermingled nanofibers, the nanofibers having diameters of about 700 nm or less, providing a biological sample comprising sperm cells from a sperm donor and epithelial cells from an epithelial cell donor, selectively digesting the epithelial cells of the sample using an epithelial cell digesting agent to form a first digest mixture, the first digest mixture including an E-fraction of digested epithelial cell DNA, and separating the sperm cells of the sample from the digested epithelial cells by filtration of the first digest mixture through the nanofiber filter, the sperm cells becoming entrapped in the nanofiber filter.

The method may further comprise digesting the sperm cells entrapped in the nanofiber filter using a sperm cell digesting agent to form a second digest mixture, the second digest mixture including an S-fraction of digested sperm cell DNA, isolating the DNA from the E-fraction, isolating the DNA from the S-fraction, generating a DNA profile for determining the identity of the sperm donor, and generating a DNA profile for determining the identity of the epithelial cell donor.

The method of the present invention may further comprise providing a first sample, the first sample being a saliva sample, a buccal sample, or a blood sample collected from a candidate sperm donor, providing a second sample, the second sample being a saliva sample, a buccal sample, or a blood sample collected from a candidate epithelial cell donor, mixing a portion of the first sample with a portion of the second sample to produce a mixture sample, generating DNA profiles corresponding to the first sample, the second sample and the mixture sample, and using the DNA profiles to determine whether the sperm donor corresponds to the candidate sperm donor and whether the epithelial cell donor corresponds to the candidate epithelial cell donor.

In the methods of the present invention for processing forensic samples, the biological sample upon which the methods operate may be a forensic sample collected according to a protocol established for a sexual assault kit.

In the methods of the present invention, the sperm cell digesting agent may be a chemical reducing agent. In some embodiments, the chemical reducing agent may be selected from the group consisting of dithiothreitol (DTT), β-mercaptoethanol (BME), glutathione (GSH) and combinations thereof. However, useful chemical reducing agents are not limited thereto.

In embodiments of the present invention, the generated DNA profiles may be of sufficient quality to be used for human identification. In certain embodiments, the DNA profiling methods of the present invention may further include searching a DNA profile database using the generated DNA profiles in order to identify the sperm donor.

The DNA profiling method of the present invention may make use of a nanofiber filter comprising nanofibers, the nanofibers being formed of at least one polymer, the at least one polymer being selected from the group consisting of a vinyl polymer, an acrylic polymer, a polyester, a polyether, a polycarbonate, a polyimide and a polycaprolactone. However, the nanofiber composition is not limited thereto, and the nanofibers may be formed of other materials including other organic polymers.

The nanofibers of the nanofiber filter ma be produced by at least one of interfacial polymerization, electrospinning and electrostatic spinning. However, methods of preparing suitable nanofibers are not limited thereto.

In the methods of the present invention, the nanofiber filter may comprise an electrospun hybrid nanofiber felt, and the electrospun hybrid nanofiber felt may comprise a composite nanofiber and a single component nanofiber.

In the methods of the present invention, a thickness of the nanofiber filter may be in a range of from about 70 µm to about 800 µm. Alternatively, a thickness of the nanofiber filter may be in a range of from about 70 µm to about 100 µm, from about 100 µm to about 200 µm, from about 200 µm to about 300 µm, from about 400 µm to about 600 µm, or from about 600 µm to about 800 µm.

In the methods of the present invention, an effectiveness of the separating step may be affected by both a pore size and a thickness of the nanofiber filter In some embodiments of the methods of the present invention, the nanofiber filter may be made of polycaprolactone nanofibers, polyimide nanofibers, carbon nanofibers, or ceramic nanofibers. However, the composition of the nanofiber filter is not limited thereto, and the nanofiber filter may be made of other organic or inorganic materials or polymers.

In certain embodiments of the present invention, the nanofiber filter may be comprised of bundles of nanofibers, the nanofibers being hollow, the nanofibers being oriented in a direction parallel to a direction of flow of the first digest mixture through the nanofiber filter.

In certain preferred embodiments of the present invention, an apparent pore size of the nanofiber filter may be less than about 2.5 µm. In other embodiments, an apparent pore size of the nanofiber filter may be less than about 3.0 µm, less than about 2.3 µm, or less than about 2.0 µm. In some embodiments, an apparent pore size of the nanofiber filter may range from about 2.4 µm to about 2.6 µm, from about 2.3 µm to about 2.5 µm, from about 2.0 µm to about 2.5 µm, or from about 2.5 µm to about 2.7 µm.

In certain embodiments, the methods of the present invention may further comprise providing a filter cartridge enclosing the nanofiber filter and using centrifugation methods to accomplish the separating step. In some embodiments, the DNA profiling methods of the present invention may further comprise enclosing the nanofiber filter in a manifold or housing and applying within the manifold or housing one or both of air pressure to a fluid entry side of the nanofiber filter and vacuum to a fluid exit side of the nanofiber filter in order to accomplish the separating step.

In certain embodiments of the methods of the present invention, the sperm cells ma be recovered with higher than about 70% efficiency. In other embodiments, sperm cells may be recovered with higher than about 50% efficiency, about 60% efficiency, about 80% efficiency, about 90% efficiency, or about 95% efficiency.

In some embodiments, the present invention may include an apparatus for processing a forensic sample including sperm cells and non-sperm cells. The apparatus may comprise a lysis chamber for selective lysing of non-sperm cells to form a first lysate, a nanofiber filter capable of entrapping sperm cells when the first lysate is passed through the filter, means for passing the first lysate from the lysis chamber onto the nanofiber filter, a first collection vessel for collecting the filtered first lysate, an enclosure including the nanofiber filter, the enclosure allowing for contact between sperm cells entrapped in the filter and a sperm lysing agent to be applied in order to form a second lysate, and a collection vessel for collecting the second lysate.

In certain embodiments, the apparatus of the present invention may be formed as a micro fabricated device, the nanofiber filter being oriented in-line with the lysis chamber and the first collection vessel.

In some embodiments, the apparatus may further comprise a capability for generating DNA profiles for both the sperm cell DNA and the non-sperm cell DNA in the sample In some embodiments, the passage of the first lysate through the nanofiber filter of the apparatus may be pressure-assisted or vacuum-assisted.

In the apparatus of the present invention, the selective lysing of non-sperm cells may be effected by a combination of a detergent and proteinase enzyme. In some embodiments, the sperm cell lysing agent may be a mixture of a detergent, proteinase enzyme and a chemical reducing agent. The chemical reducing agent may be one of dithiothreitol (DTT) and β-mercaptoethanol, but it is not limited thereto.

In certain embodiments, the apparatus of the present invention may allow for the isolation of sperm cell DNA and non-sperm cell DNA from the sample and subsequent DNA analysis and human identification.

In certain embodiments, an apparatus of the present invention for processing forensic samples for human identification may comprise an automated robotic platform that is capable of using a nanofiber filter device to separate one of sperm cells and sperm cell DNA from one of non-sperm cells and non-sperm cell DNA.

In certain embodiments, the present invention may include a kit for processing forensic samples. The kit may comprise a plurality of cup-shaped nanofiber filters, each filter held within a standard centrifuge spin column, each filter comprising intermingled nanofibers, the nanofibers having diameters of about 700 nm or less, a digest buffer comprising a buffer material for maintaining a solution pH in a physiological range, a chelating, agent, a surfactant and a cell digesting enzyme, a cell digesting enzyme solution to aid in cell digestion, a chemical reducing agent for lysing sperm cells, an eluting buffer solution comprising a buffer material for maintaining a solution pH in a physiological range, the eluting buffer being useful as an eluting solvent in purifying DNA, a DNA isolation kit, an InnoQuant™ kit for quantitating DNA and instructions for processing forensic samples. The nanofiber filters of the kit need not be cup-shaped, but may be disc-shaped, cone-shaped, or square-shaped, or may have another suitable shape.

The kit for processing forensic samples may include a digest buffer, and the digest buffer may comprise tris(hydroxymethyl)aminomethane ethylenediamine tetraacetic acid (EDTA), sodium dodecyl sulfate (SDS) and proteinase K. However, the digest buffer composition is not limited thereto.

The kit for processing forensic samples may include a chemical reducing agent for lysing sperm cells, and the chemical reducing agent may be selected from the group consisting of dithiothreitol (DTT), β-mercaptoethanol (BME), glutathione (GSH) and combinations thereof. However, the chemical reducing agent for lysing sperm cells is not limited thereto.

The kit for processing forensic samples may include an eluting buffer solution comprising a buffer material for maintaining a solution pH in a physiological range, and the eluting buffer may comprise tris and EDTA (TE buffer). However, the eluting buffer material is not limited thereto, and, in certain embodiments, the eluting buffer material may comprise a buffer material capable of maintaining the eluting solvent pH in a physiological range and a metal chelating agent.

The kit for processing forensic samples may include a cell digesting enzyme solution to aid in cell digestion, and the cell digesting enzyme solution may be proteinase K (20 mg/L).

The kit for processing forensic samples may comprise a nanofiber filtration device that is capable of isolating sperm cells or sperm DNA from one of epithelial cells and non-sperm cell DNA.

The methods, apparatus and kit of the present invention may be used with classical filter cartridges and centrifugation based methods. These methods may easily be adapted to automation and high throughput processing with robotic systems having a vacuum manifold or with a micro fabricated device using a flow-through nanofiber filter.

DETAILED DESCRIPTION OF THE INVENTION

Figure 1:
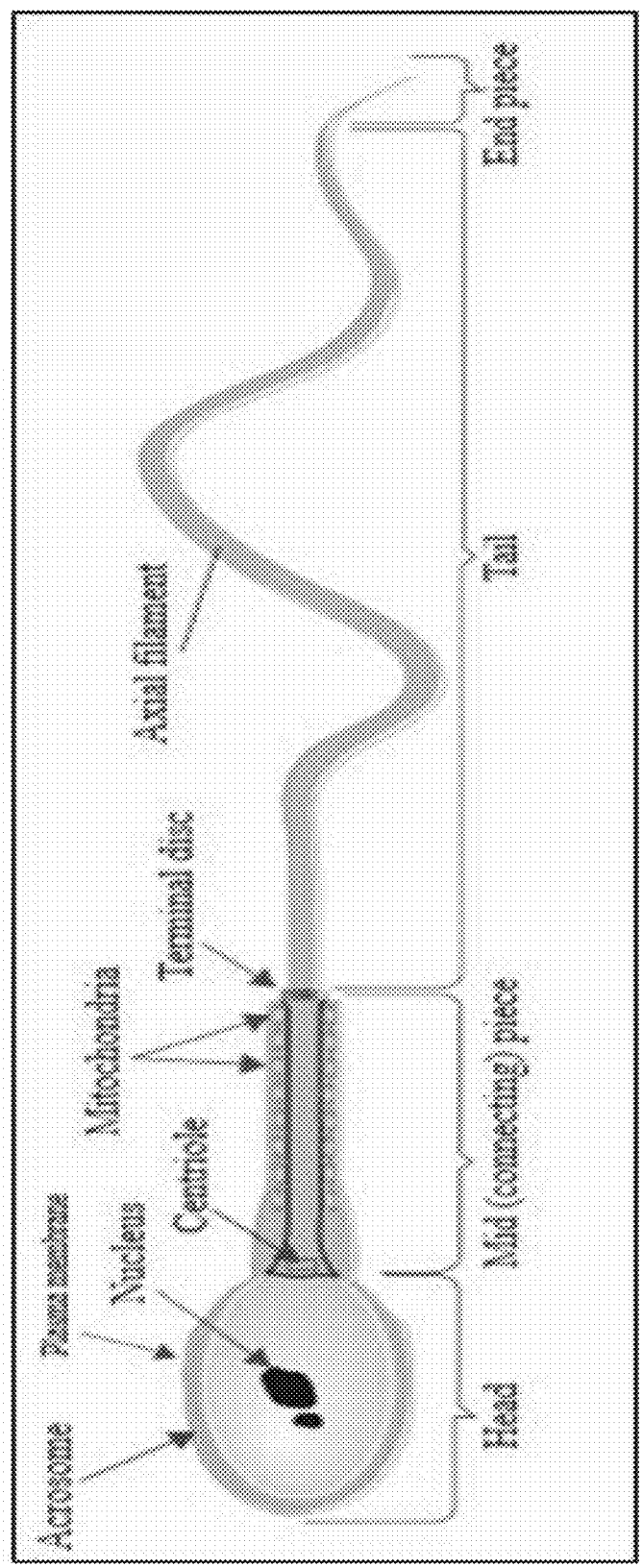
FIG. 1 shows the structure of an intact sperm cell.

Of utmost importance in a forensic sexual assault case is the ability to separate sperm cells from other cells present in the sample matrix, thereby producing a dean sperm cell fraction. The DNA profile of the sperm cell fraction will clearly identify the perpetrator(s). Intact sperm cells have the structure depicted in FIG. 1. In most forensic samples, the sperm is degraded and only the head portion remains intact. The mean sizes of human sperm are reported as: length: 437 μm and width: 275 μm (G. Bellastella, et al., *Dimensions of human ejaculated spermatozoa in Papanicolaou stained seminal and swim-up smears obtained from the Integrated Semen Analysis System (ISAS®)*, Asian Journal of Andrology 12(6): 871-879 (2010)). The strong disulfide bonds present on the cell surface proteins of sperm cells makes them resistant to mild protease digestion. Hence when a mild proteinase digestion is performed in a forensic sample containing sperm cells and other skin cells such as epithelial cells from a rape examination swab, all other cell types digest, releasing the DNA; whereas the sperm cell acrosome containing male DNA remains intact. After the sperm cells are pelleted by centrifugation, the soluble DNA from the epithelial and non-sperm cells is removed in the supernatant, and this becomes known as the "epithelial" or "non-sperm" fraction. The sperm cells may then be washed three times to remove any remaining DNA from the non-sperm cells. Then the sperm cells are digested using a reducing agent chemical such as DTT to break the protein disulfide bonds and a proteinase enzyme such as proteinase K to digest the sperm cells. This methodology, commonly referred to as differential digest, works well and is capable of cleanly separating the male DNA profile from the female DNA profile used for identification of the sperm donor and the sexual assault victim associated with a sexual assault evidence sample.

The present invention uses the similar proven differential digest chemistry, but utilizes a unique methodology for the separation of the sperm cells from the digested DNA of non-sperm cells. The unique properties of nanofiber filters (layers of nanofibers) allow separation of the sperm cells not only based on actual pore size but on the layers of the nanofiber filter that create a web like structure to trap the sperm cells without clogging the filter and with high flow rate. The results herein demonstrate that as high as 89% percent of the sperm cell DNA can be recovered after filtration through the nanofiber filter. The results also indicate that the yield can be further improved by creating nanofiber filters with materials which do not bind DNA by adsorption and have optimal thickness and pore size. It is also demonstrated that in a simulated rape examination swab containing a mixture of both epithelial and sperm cells, the method can separate the DNA of the two types of cells, and the resulting DNA profiles can be used by the criminal justice system to identify the sperm donor associated with sexual assault evidence. The method of the present invention makes use of these polymer filters for separation of sperm cells from other contaminant non-sperm cells in a forensic sample by using a nanofiber filter as a filtration medium.

For the purposes of the present invention, a nanofiber is a slender and greatly elongated filament having a diameter of up to about 700 nm. A nanofiber filter is a mat comprising randomly overlaid or intermingled nanofibers, where gaps between the nanofibers form pores, the pores being interlinked to form tortuous pathways through the nanofiber filter mat. The nanofiber filter mat has an apparent pore size corresponding to its apparent maximum pore diameter.

EXAMPLES

Example 1

Detailed Extraction Protocol Showing the Efficiency of Capturing Intact Sperm Cells on Nanofiber Filters, Recovery of Digested Sperm Cell DNA, and Evaluation of the Utility of the Method for Forensic DNA Analysis of Dried Mock Vaginal Swabs This Example demonstrates the efficacy of nanofiber filters for clean separation of epithelial cells from sperm cells found in a simulated forensic case sexual assault swab. Nanofiber filters of polycaprolactone nanofiber extracellular matrix (ECM PCL) having two different thicknesses, 500 µm and 600 µm (hereinafter 'Fiber 1' and 'Fiber 2', respectively), were used. A comparison of the efficiency of separation and recovery of sperm DNA by the two filters having different thicknesses is provided. The two types of nanofiber filters were evaluated using a simulated rape kit swab for the efficiency as well as the efficacy of separation of the sperm and non-sperm cell mixture by nanofiber filters.

A simulated rape examination swab was created by adding sperm cells to epithelial (buccal) cells from two different individuals. Sperm were initially washed, and extraneous non-sperm cells removed through mild digestion (using Proteinase K, hereinafter 'PK'). The washed sperm cells were mixed with epithelial cells (from a cheek swab) in 1:1 ratio. A small fraction of these unfiltered cells were removed before separation for use as a control mixture sample. (Alleles from both donors are expected in this control sample.) The remaining portion of the cell mixture was subjected to partial digestion with the expectation that epithelial DNA would be freed from the lysed epithelial cells and sperm cells would remain intact. Epithelial DNA plus sperm cell mixtures were filtered through different nanofiber filters. These mixtures were added in small volume directly to the nanofiber filter "cups". Epithelial DNA within the flow-through was stored (referred to as the epithelial fraction), and sperm cells trapped on nanofibers were subjected to complete digestion. An additional digestion with DTT was performed to the flow through. This procedure revealed the extent to which sperm cells were not retained by the nanofiber and entered the flow-through. The AmpF ℓ STR® Identifier® Plus PCR Amplification Kit from Life Technologies was used to determine the source of the DNA in each fraction. (Sperm and epithelial cells were from two distinct individuals and thus had two distinct male profiles.) The sperm samples were subjected to mild digestion to remove any cell debris or epithelial cells from the sperm donor so that the quantification of DNA from the lysates after separation would give a correct measure of efficiency of separation.

Figure 2:
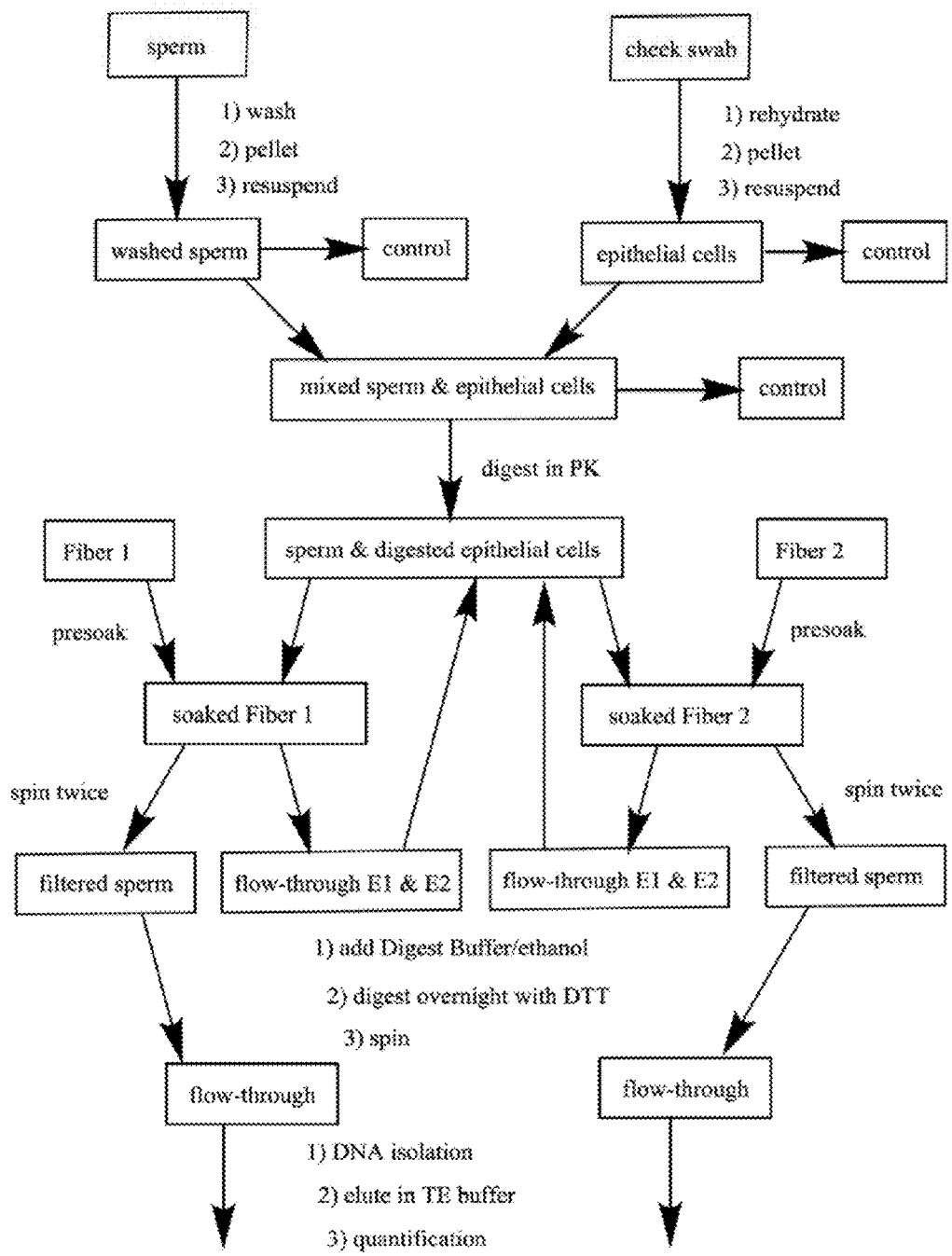
FIG. 2 is a flow chart depicting the Detailed Extraction Protocol used for processing a simulated rape examination swab to test two nanofiber filters.

The Detailed Extraction Protocol for processing the simulated rape examination swab is illustrated in the flow chart presented as FIG. 2 and was as follows:

Step 1: Wash neat sperm (40 µL) in 1 mL 1× PBS (phosphate buffer saline).

Step 2: Pellet sperm cells and additional cells that may be present in the ejaculate (epithelial cells, white blood cells, etc.) for 5' at 10,000 rpm using an Eppendorff MiniSpin® centrifuge, which produces approximately 6,700 g at this speed. The Eppendorf MiniSpin® centrifuge was used for all centrifugation steps described in this disclosure.

Step 3: Re-suspend cell pellet in 20 µL Digest Buffer.

Step 4: Rehydrate epithelial cells on cheek swab by breaking swab into 1 mL 1× PBS and let sit for 30-60min.

Step 5: Vortex swab in PBS and pellet cells for 5' at 10,000 rpm.

Step 6: Re-suspend epithelial cells in 110 µL Digest Buffer (10 mM tris(hydroxymethyl)aminomethane, 10 mM ethylenediamine tetraacetic acid (EDTA), 50 mM NaCl, 2% sodium dodecyl sulfate (SDS) at pH=7.5).

Step 7: Mix epithelial and sperm cells in given volume ratios: 1:1-10 µL epithelial+10 µL sperm+90 µL Digest Buffer.

Step 8: Remove 10 µL from each mixture (Pre separation control sample): AG121.

Step 9: Add 2.5 µL proteinase K (PK) (20 mg/mL) to remaining 100 µL mixture and digest for 1 hour at 56° C. to digest epithelial cells only.

Step 10: Pre-soak nanofibers by adding 5 µL of Digest Buffer directly onto each nanofiber "cup".

Step 11: Add 50 µL digest mixture (from Step 9) into each of the appropriate nanofiber filters and spin for 1' at 1,000 rpm. The nanofiber filters were spun a second time due to the liquid not flowing through in its entirety. The second spin was performed for 1' at 3,000 rpm. This is the second flow through. Store 25 µL of this digest. Together, this is the PK flow through, or "E PK" fraction AG115/119).

Step 12: Take the remaining volume of the E_PK digest flow through and add 5 µL PK and 10 µL DTT to it. This second flow through is the E_PK+DTT digest (AG107/111) and along with the epithelial cells that flowed through, will contain any lysed sperm cells that may have flowed through as well.

Step 13: Place nanofiber into fresh tube with 200 µL Digest Buffer, 5 µL PK and 10 µL dithiothreitol (DTT)

Step 14: Digest overnight at 56° C.

Step 15: Remove nanofiber filter into a fresh basket/Eppendorf tube and centrifuge at 5,000 rpm for 1' to collect DNA from soaked filter. This is the sperm fraction and will contain the digested sperm cells that remained on the filter (AG103).

Step 16: Add ethanol in 1:1 volume with Digest Buffer and proceed to BioBasic mini-prep genomic DNA isolation kit (Bio Basic Inc., Amherst, N.Y.).

Step 17: Elute in 50 µL DNA suspension buffer (TE).

Step 18: Proceed to DNA quantification using Inno-Quant™ kit (InnoGenomics Technologies, LLC, New Orleans, La.). The InnoQuant™ kit allows for separate quantitation of male DNA and female DNA for each fraction.

The recovered DNA was then amplified using the AmpF ℓSTR® Identifier® Plus PCR Amplification Kit from Life Technologies following manufacturer's standard DNA analysis protocols. The results were analyzed on an Applied Biosystems® 3130 Genetic Analyzer using Genemapper® ID-X or Genemapper software following standard protocols and using a minimum RFU threshold of 100 RFU.

As described above, a simulated rape examination swab was created try adding sperm cells to buccal cells from two different individuals. The swab was processed according to the Detailed Extraction Protocol using NanoECM™ PCL Fiber 1 and Fiber 2 (Nanofiber Solutions, Columbus, Ohio). The recovery yields are shown in Table 1 as quantitation values for the resultant sperm and epithelial fractions from Fiber 2. The DNA quantitation values found in the sperm fractions confirm that DNA is successfully recovered from all tested nanofiber filters. In order to determine the efficacy of each filter to trap sperm cells, the quantity of DNA in the nanofibrous fraction is divided by the combined total DNA recovered from the nanofiber filter and flow-through fractions, and the result is given as a recovery percentage. For the two tested samples (A and B), Fiber 1 captured sperm cells at 11% and 32%, respectively. For the two tested samples (A and B), Fiber 2 captured sperm cells at 76% and 89%, respectively. Fiber 2 captured sperm cells at a higher efficiency. This experiment clearly established the high efficacy of the nanofibrous filter to capture sperm cells.

DNA is successfully recovered from the filter. The robust DNA quantitation values found in the sperm fractions confirm that DNA is successfully up to 89% recovered from the nanofiber. Through the use of controls, the fact that the nanofiber filter itself does not contribute any contaminating DNA was confirmed. The observed DNA yield can be further improved by optimizing the extraction process and filter composition.

Epithelial DNA effectively flows through nanofibers. Epithelial DNA was quantified in the flow-through fractions, indicating that epithelial DNA effectively passes through the nanofiber. The amount of epithelial DNA recovered varied between samples. This protocol uses low spin speeds in order to separate epithelial DNA from intact sperm cells. The separation efficiency was investigated by measuring the amount of DNA present in the flow-through of a single wash step. The majority of epithetial DNA is recovered after the first low speed spin. Only small amounts of epithelial DNA are trapped within the nanofiber after the wash step (5-15% of total epithelial DNA recovered). The results indicate that the nanofiber filters can effectively separate the undigested sperm cells from the digested epithelial cell DNA without clogging the filter and with a high flow rate.

TABLE 1

DNA quantitation values using InnoQuant™ of simulated sexual assault swabs for Sample A and Sample B with Fiber 2

| ID | Protocol Step | Sample | Digest | Fraction | Mean Quant (ng/μL) | Epith. (μL) | Sperm (μL) | ng DNA | Fractional recovery of sperm cell DNA on filter |
|---|---|---|---|---|---|---|---|---|---|
| AG121 | 8 | A | PK + DTT | Unfiltered | 0.53 | 0.91 | 0.91 | 133.11 | |
| AG115/119 | 11 | A | PK Flow Through | E_PK | 0.04 | 4.55 | 4.55 | 2.36 | |
| AG107/111 | 12 | A | PK + DTT Flow Through | E_PK + DTT | 0.44 | 4.55 | 4.55 | 23.34 | |
| AG103 | 15 | A | PK + DTT | Nanofiber (Sperm) | 1.59 | 4.55 | 4.55 | 79.68 | 76% |
| AG116/120 | 11 | B | PK Flow Through | E_PK | 0.17 | 45.45 | 4.55 | 12.22 | |
| AG108 | 12 | B | PK + DTT Flow Through | E_PK + DTT | — | 45.45 | 4.55 | 3.67 | |
| AG104 | 15 | B | PK + DTT | Nanofiber (Sperm) | 2.51 | 45.45 | 4.55 | 125.27 | 89% |

Example 2

Analysis of Isolated Sperm Cell DNA and Epithelial Cell DNA Using a Forensic STR DNA Analysis Kit The recovered DNA was amplified using the AmpF ℓSTR® Identifier® Plus PCR Amplification Kit following the manufacturer standard DNA analysis protocols. The extraction control, a negative control and a positive control DNA were analyzed with the isolated sperm cell DNA and epithelial cell DNA samples. The profiles of the known reference samples were generated as well as the profiles of the mixture samples prior to differential digestion and subjected to nanofiber filter separation as control results for comparison purposes.

Table 2 shows the DNA profiles obtained from samples A and B using the Fiber 2 nanofiber filter and Table 3 shows the DNA profiles obtained from samples A and B using the Fiber 1 nanofiber filter. From this data, it is evident that the corresponding donor is correctly detected as the major component of each respective fraction irrespective of the fiber used (Fiber 1 or Fiber 2), and irrespective of whether sample A or sample B was tested. For example, the sperm cell donor is the major donor in all sperm fractions tested, with very little contribution from the epithelial donor.

TABLE 2

Identifiler Plus ® results for Fiber 2 with Sample A and Sample B. Alleles with a peak height of less than 50% of the main peak in each locus are designated as weak alleles and are placed in parentheses.

| Marker | Sperm Reference | Epithelial Reference | Unfiltered Sample B (AG122) | Sperm Fraction Sample B (AG104) | Sperm Fraction Sample A (AG103) | Epithelial Fraction Sample B (AG116) |
|---|---|---|---|---|---|---|
| D8S1179 | 13, 16 | 10, 12 | (10, 12), 13, 16 | (10, 12), 13, 16 | 13, 16 | 10, 12 |
| D21S11 | 30, 32.2 | 29, 30 | (29), 30, 32.2 | (29), 30, 32.2 | 30, 32.2 | 29, 30 |
| D7S820 | 11 | 11 | 11 | 11 | 11 | 11 |
| CSF1PO | 9, 10 | 10 | 9, 10 | 9, 10 | 9, 10 | 10 |
| D3S1358 | 16 | 14, 16 | (14), 16 | (14), 16 | 16 | 14, 16 |
| TH01 | 7, 9.3 | 6, 7 | (6), 7, 9.3 | 7, 9.3 | 7, 9.3 | 6, 7, (9.3) |
| D13S317 | 12 | 11, 12 | (11), 12 | 12 | 12 | 11, 12 |
| D16S539 | 8, 11 | 12 | 8, 11, (12) | 8, 11, (12) | 8, 11 | 12 |
| D2S1338 | 23, 24 | 22, 25 | (22), 23, 24, (25) | (22), 23, 24 | (22), 23, 24 | 22, (23, 24), 25 |
| D19S433 | 13, 14 | 14 | 13, 14 | 13, 14 | 13, 14 | (13), 14 |
| vWA | 17, 18 | 16, 18 | 16, 17, 18 | 17, 18 | 17, 18 | 16, (17), 18 |
| TPOX | 8 | 8, 11 | 8, (11) | 8 | 8 | 8, 11 |
| D18S51 | 14, 15 | 12, 18 | (12), 14, 15, (18) | 14, 15 | 14, 15 | 12, 18 |
| AMEL | X, Y | X, Y | X, Y | X, Y | X, Y | X, Y |
| D5S818 | 12 | 12 | 12 | 12 | 12 | 12 |
| FGA | 19, 21 | 21, 25 | 19, 21, (25) | 19, 21 | 19, 21 | 21, 25 |

TABLE 3

Identifiler Plus ® results for Fiber 1, Samples A and B. Alleles with a peak height of less than 50% of the main peak in each locus are designated as weak alleles and are placed in parentheses.

| Marker | Sperm Reference | Epithelial Reference | Unfiltered Sample B (AG122) | Sperm Fraction Sample B (AG101) | Sperm Fraction Sample A (AG102) | Epithelial Sample B (AG114) |
|---|---|---|---|---|---|---|
| D8S1179 | 13, 16 | 10, 12 | (10, 12), 13, 16 | (10, 12), 13, 16 | (10, 12), 13, 16 | 10, 12 |
| D21S11 | 30, 32.2 | 29, 30 | (29), 30, 32.2 | (29), 30, 32.2 | (29), 30, 32.2 | 29, 30 |
| D7S820 | 11 | 11 | 11 | 11 | 11 | 11 |
| CSF1PO | 9, 10 | 10 | 9, 10 | 9, 10 | 9, 10 | (9), 10 |
| D3S1358 | 16 | 14, 16 | (14), 16 | (14), 16 | 16 | 14, 16 |
| TH01 | 7, 9.3 | 6, 7 | (6), 7, 9.3 | (6), 7, 9.3 | 7, 9.3 | 6, 7, (9.3) |
| D13S317 | 12 | 11, 12 | (11), 12 | (11), 12 | 12 | 11, 12 |
| D16S539 | 8, 11 | 12 | 8, 11, (12) | 8, 11, 12 | 8, 11, (12) | (11), 12 |
| D2S1338 | 23, 24 | 22, 25 | (22), 23, 24, (25) | (22), 23, 24, (25) | 23, 24 | 22, (23, 24), 25 |
| D19S433 | 13, 14 | 14 | 13, 14 | 13, 14 | 13, 14 | (13), 14 |
| vWA | 17, 18 | 16, 18 | 16, 17, 18 | 16, 17, 18 | (16), 17, 18 | 16, 18 |
| TPOX | 8 | 8, 11 | 8, (11) | 8, (11) | 8 | 8, 11 |
| D18S51 | 14, 15 | 12, 18 | (12), 14, 15, (18) | (12), 14, 15, (18) | 14, 15 | 12, 18 |
| AMEL | X, Y | X, Y | X, Y | X, Y | X, Y | X, Y |
| D5S818 | 12 | 12 | 12 | 12 | 12 | 12 |
| FGA | 19, 21 | 21, 25 | 19, 21, (25) | 19, 21, (25) | 19, 21, (25) | 21, 25 |

Figure 3:
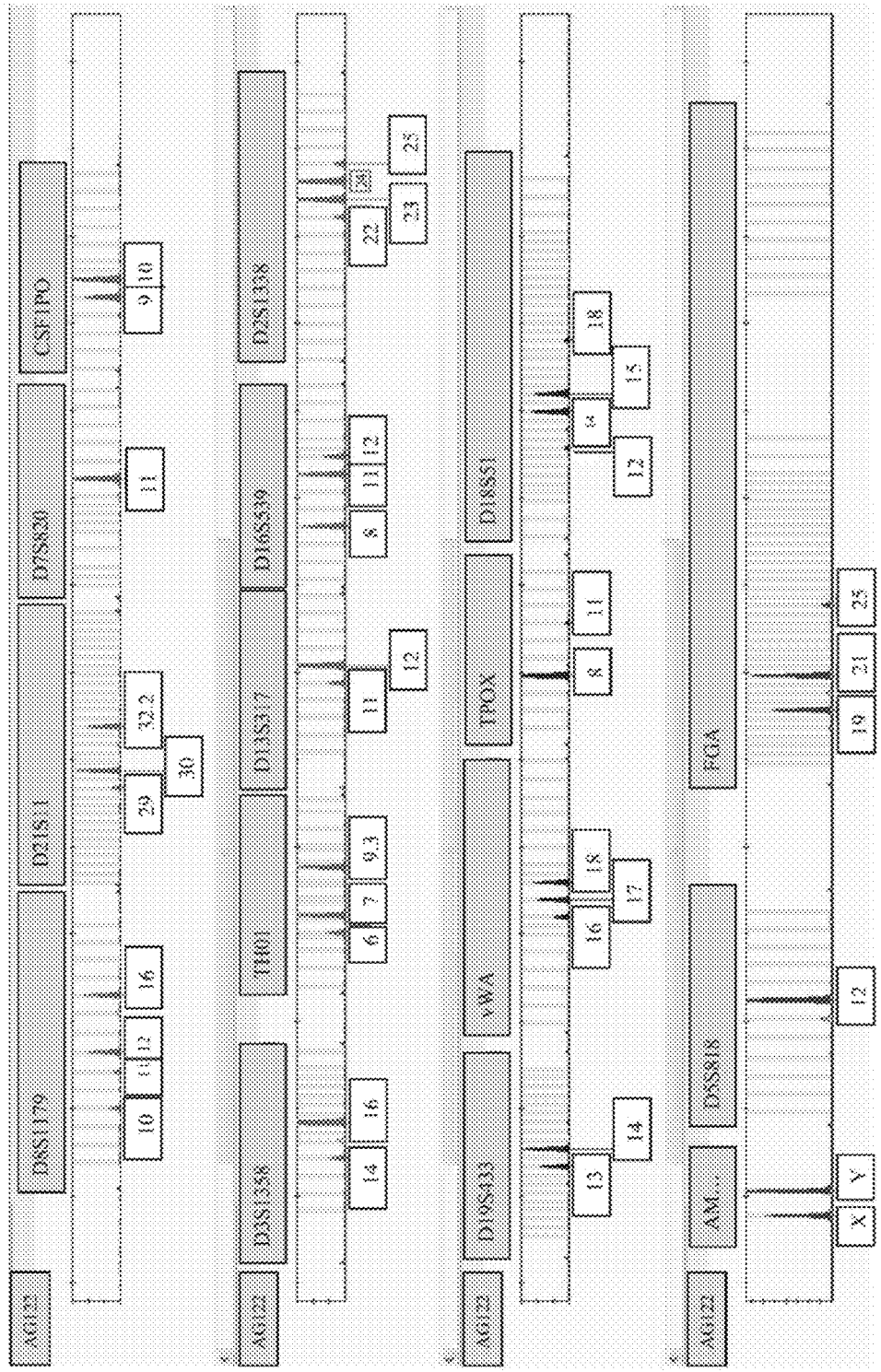
FIG. 3 shows the DNA profile of the mixed epithelial and sperm sample B cell mixture sample prior to isolation using the nanofiber. As expected, this DNA profile is a mixture of the two known donors.

FIG. 3 shows the DNA profile prior to isolation using the nanofiber of sample B. As expected, this DNA profile is a mixture of the two known donors.

Figure 4:
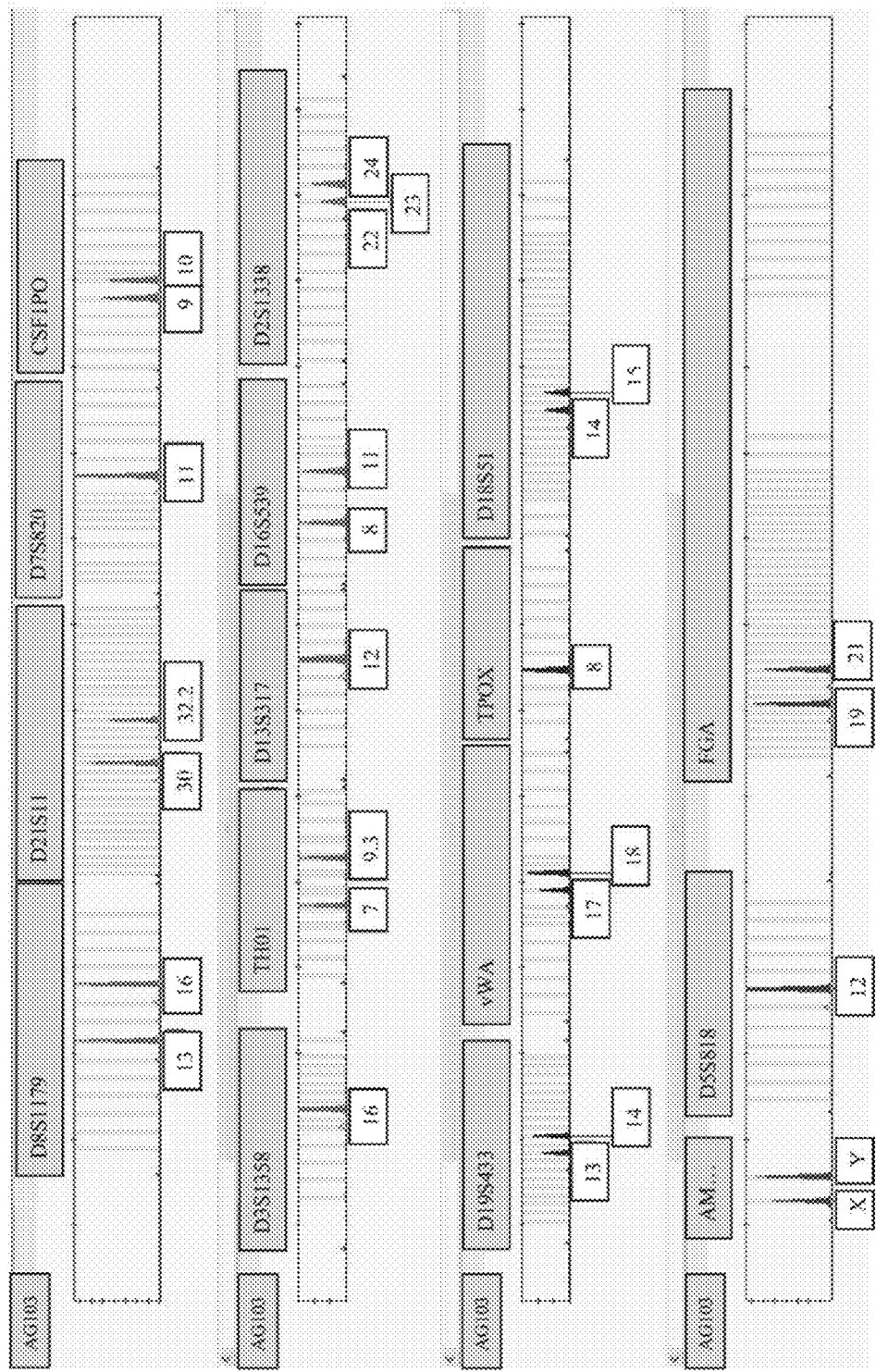
FIG. 4 shows the Identifier® Plus STR DNA profile of an isolated sperm cell fraction after separation by Fiber 2, a filter having a thickness of 500 μm. The Y scale is zoomed in to 1500 RFU.

FIG. 4 shows the DNA profile of the sperm fraction after separation using Fiber 2. The sperm fraction obtained from Fiber 2 produced a DNA profile consistent with the known sperm donor as the major contributor, with the epithelial donor being detected as a minor component at only 1 marker in the sample A mixture swab. This result is highly desirable in a forensic case, enabling simple result interpretation of a single male donor, and therefore, simple presentation to a jury in a court of law.

Figure 5:
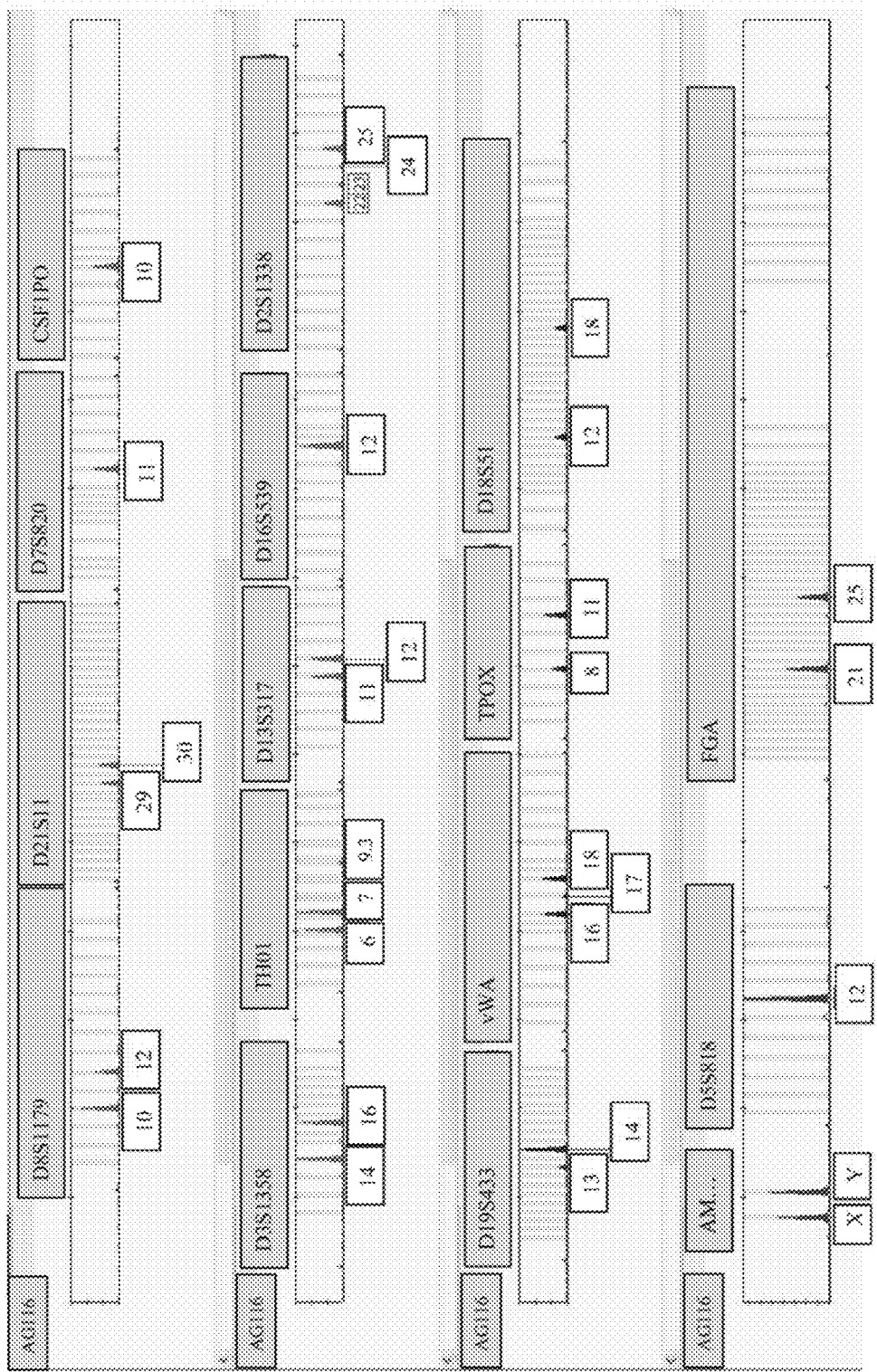
FIG. 5 shows the Identifier® Plus STR DNA profile of an isolated epithelial cell fraction alter separation by Fiber 2, a filter having a thickness of 500 μm. The Y scale is zoomed in to 1500 RFU.

FIG. 5 shows the DNA profile of the epithelial fraction after separation using Fiber 2. The epithelial fraction exhibits a mixture of the epithelial donor and the sperm donor at 4 of the 15 markers tested. The epithelial donor is the major contributor in the epithelial profile, with alleles from the sperm donor being detected as a minor component at only 4 markers.

Regarding the probative fractions of interest, the sperm fractions, Fiber 2 performed more effectively in yielding a clean sperm profile than Fiber 1. The sperm fractions obtained from Fiber 2 produced a DNA profile consistent with the known sperm donor as the major contributor, with the epithelial donor being detected as a minor component at only 5 of 15 markers in the sample B mixture swab and only 1 marker in the sample A mixture swab. The sperm fractions obtained from Fiber 1 produced a DNA profile consistent with the known sperm donor as the major contributor, with the epithelial donor being detected at all 15 markers in the sample B mixture swab and at only 5 markers in the sample A mixture swab. It is observed that Fiber 2 was more effective in producing clean sperm profiles. The results indicate that the nanofiber filters can effectively separate the undigested sperm cells from the digested epithelial cell DNA. It is noted that the sperm fraction is the most probative fraction, which, in a sexual assault case, identifies the sperm donor in the sexual assault evidence.

Differentiation of the Present Invention from Prior Art:

Density medium based separation: Although this process is commercially available, it is still not easy to perform and clean sperm DNA separation/recovery can be variable and sub-optimal. The method is much more complex than the manual method to automate. The reason for the sub-optimal clean sperm DNA recovery of this method is any of the victim's epithelial cell DNA that remains in particulate form, due to incomplete digestion of the victim's cells, will contaminate the male DNA fraction purified using this method, yielding a mixture of male and female DNA in the sperm fraction. In comparison, nanofiber filters are easily automatable and simple to use, yielding reproducible and consistent results without any victim epithelial cell contamination in the sperm profile. This is because the sperm is trapped in the nanofiber, and all lysed victim epithelial cells will go through the filter. Therefore, nanofiber filters are a novel, unique way of obtaining a clean sperm fraction in the presence of contaminating victim epithelial cells.

Immunological or other affinity based methods: This method is dependent on having intact sperm cells, which is a rare in a forensic case. Most forensic samples contain degraded cells due to the harsh environmental conditions samples are exposed to, or simply due to the passage of time. In this method, degraded protein from sperm cells may block the binding site of the antibody, making the binding unsuccessful. This interferes with the separation and is the reason why this method is not commercially successful. The affinity based approach previously suggested by Sinha uses other sperm binding proteins, but is subject to the same limitations as affinity binding due to protein debris present in the sample. On the other hand, nanofiber separation does not depend on affinity binding, but on size separation. In the examples provided, it is shown that any degraded cellular debris is digested and goes through the filter into the epithelial fraction, leaving a clean sperm fraction, providing a clean, single source sperm DNA profile, easily identifying a perpetrator. Therefore, the novel nanofiber filtration method of separation is not adversely affected by the presence of degraded cells in a forensic sample.

Laser microdissection: Although this method leads to a clean sperm fraction, it depends on a costly microscope and supplies, complicated collection methods different from those currently used, and is not amenable to high throughput processing. This method is time-consuming and labor-intensive (to identify the sperm cells in the sample). The novel approach of nanofiber separation is low cost, automatable, and can be easily adapted to high throughput processing (i.e. in a 96-well plate format).

Microfluidic based methods: This method works well for intact sperm, but is labor intensive, requires high cost and complex engineering design, and is not currently commercially available due to these reasons. On the other hand, the novel approach of nanofibers separation can easily be amenable to automation by creating a 96-well plate platform, and using a liquid handler robot equipped with vacuum manifold capabilities. There is no complex engineering design or high cost, and an automatable method, by definition, requires very little labor effort.

DNAse digestion based method: Although this method is commercially available, the fear of introducing a DNA degrading enzyme into valuable forensic DNA samples that are already limited in quality and quantity commonly found in a forensic laboratory is not appealing to forensic scientists. Therefore, this method is available, but not widely accepted. The proposed novel nanofiber separation, however, does not depend on chemical separation means, but on the physical properties of the nanofibers. There is no use or introduction of any chemicals that can be detrimental to forensic samples and will therefore be widely accepted in the forensic field.

Selectively lysing the sperm cells: The method described by Liu, *Selective lysis of sperm cells,* EP 2115123 A2 (published 11 Nov. 2009), lyses the sperm cells, leaving epithelial cells intact. It does not use any specific separation method other than chemical lysis. The Nanofiber method is novel and unique in terms of its ability to isolate clean sperm cell DNA from a forensic rape evidence collection kit and provide ability to obtain DNA profile to identify the sperm donor.

Physical separation by filtration based methods (nylon filters and track etched filters of defined pore size): This method is most similar to the proposed method of using filtration to separate cells, but instead retains un-lysed victim epithelial cells in the nylon or track etched filter and allows the sperm to pass through. This method thus suffers from the same limitations as density medium based separation, which is the contamination of the sperm cell lysate with degraded or lysed victim epithelial or non-sperm cells, resulting in a sperm fraction contaminated with non-sperm DNA. Another drawback of all other filtration methods that have been proposed or used for forensic samples is the susceptibility to clogging of the filter by the excess of non-sperm cells, thereby not allowing the sperm cells to flow through and obtaining very low yields of sperm cell DNA. On the other hand, nanofiber separation is novel, unique and superior to other filter based separation methods due to the various properties of nanofibers that can be used to design an optimal filter that will only retain sperm cells, and not any other non-sperm cells or cellular debris present in the sample. The filter material and the thin thread diameter gives nanofiber filters their unique and novel property because the small fiber dimensions provide increased surface area and controlled pore size. By combining various materials, thread diameter, pore size and filter thickness, the highest flexibility is gained to design the best filter that will retain only sperm cells, thereby yielding, a clean, single source sperm fraction containing only the perpetrators' DNA profile, which is the most desirable outcome in a forensic criminal sexual assault case.

In summary, the use of nanofibers allows for effective separation of epithelial and sperm cell fractions from a rape kit simulated sample. Profiles for both epithelial and sperm cell fractions are consistent with the reference profiles of the epithelial and sperm donors, respectively, as well as the profile generated from the unfiltered mixed sample. The sperm cell profiles generated by both Fiber 2 and Fiber 1 were of a quality appropriate for court presentation and generated probative sperm fraction results of a quality superior to that of any method currently used by crime laboratories throughout the world. These results indicate that the nanofibers made from different filter thicknesses can be utilized for separation of sperm cells from epithelial cells. The efficiency of separation is dependent upon selection of the proper thickness of the nanofiber filter. The nanofiber filter having a 500 µm thickness (Fiber 1) provided 89% efficiency of collection of sperm cells from mixed samples, whereas the nanofiber filter having a 600 µm thickness (Fiber 2) provided an approximately 32% recovery of sperm cells. The tested nanofiber filter of 500 µm thickness produced a clean separation of the sperm cell DNA profile from the non-sperm cell DNA profile. The results also indicate that nanofibers of appropriate thickness from a variety of materials can be used to create a filter which can be used for the differential digest application of separating the sperm cells from a mixture of the epithelial or other non-sperm cells. The nanofiber separation, and the efficiency of recovery of valuable sperm sample crime scene evidence after separation, is not based solely on the pore size of the filter but on a combination of pore size and thickness. In comparison with other types of filters, the elevated surface area of nanofibers within a nanofiber sperm filtration system provides a more tortuous path and a greater chance to intercept sperm cells from the mixture to be filtered, while maintaining high porosity. The present invention utilizes this unique property of nanofibers for human identity application.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for processing forensic samples, the method comprising:
   providing a nanofiber filter, the nanofiber filter comprising intermingled nanofibers, the nanofibers having diameters of about 700 nm or less;
   providing a biological sample comprising sperm cells from a sperm donor and epithelial cells from an epithelial cell donor;
   selectively digesting the epithelial cells of the biological sample by using an epithelial cell digesting agent to form a first digest mixture, the first digest mixture including an E-fraction of digested epithelial cell DNA; and
   separating the sperm cells of the biological sample from the digested epithelial cells by filtration of the first digest mixture through the nanofiber filter, the sperm cells becoming entrapped in the nanofiber filter.

2. The method of claim 1, the method further comprising:
   digesting the sperm cells entrapped in the nanofiber filter using a sperm cell digesting agent to form a second digest mixture, the second digest mixture including an S-fraction of digested sperm cell DNA;
   isolating the DNA from the E-fraction;
   isolating the DNA from the S-fraction;
   generating a DNA profile for determining the identity of the sperm donor; and
   generating a DNA profile for determining the identity of the epithelial cell donor.

3. The method of claim 2, the method further comprising:
   providing a first sample, the first sample being a saliva sample, a buccal sample, or a blood sample collected from a candidate sperm donor;
   providing a second sample, the second sample being a saliva sample, a buccal sample, or a blood sample collected from a candidate epithelial cell donor;
   mixing a portion of the first sample with a portion of the second sample to produce a mixture sample;
   generating DNA profiles corresponding to the first sample, the second sample and the mixture sample; and
   using the DNA profiles to determine whether the sperm donor corresponds to the candidate sperm donor and whether the epithelial cell donor corresponds to the candidate epithelial cell donor.

4. The method of claim 3, the biological sample being a forensic sample collected according to a protocol established for a sexual assault kit.

5. The method of claim 2, the sperm cell digesting agent being a chemical reducing agent.

6. The method of claim 5, the chemical reducing agent being selected from the group consisting of dithiothreitol (DTT), β-mercaptoethanol (BME), glutathione (GSH) and combinations thereof.

7. The method of claim 2, the DNA profiles being of sufficient quality to be used for human identification.

8. The method of claim 2, further comprised of identifying the sperm donor by searching a DNA profile database using the generated DNA profiles.

9. The method of claim 1, the nanofibers of the nanofiber filter being formed of at least one polymer, and at least one polymer being selected from the group consisting of a vinyl polymer, an acrylic polymer, a polyester, a polyether, a polycarbonate, a polyimide, a cellulose and a polycaprolactone.

10. The method of claim 1, the nanofibers being produced by at least one of interfacial polymerization, electrospinning, electrostatic spinning, melt-blowing, bicomponent fiber spinning, phase separation, template synthesis and self-assembly.

11. The method of claim 1, the nanofiber filter comprising an electrospun hybrid nanofiber felt, the electrospun hybrid nanofiber felt comprising a composite nanofiber and a single component nanofiber.

12. The method of claim 1, a thickness of the nanofiber filter being in a range of from about 70 µm to about 800 µm.

13. The method of claim 1, the nanofiber filter being made of polyimide nanofibers, a thickness of the nanofiber filter being in a range of from about 400 µm to about 600 µm.

14. The method of claim 1, an effectiveness of the separating step being affected by both a pore size and a thickness of the nanofiber filter.

15. The method of claim 1, the nanofiber filter being formed of polycaprolactone.

16. The method of claim 1, the nanofiber filter being comprised of bundles of nanofibers, the nanofibers being hollow, the nanofibers being oriented in a direction parallel to a direction of flow of the first digest mixture through the nanofiber filter.

17. The method of claim 1, an apparent pore size of the nanofiber being less than about 2.5 µm.

18. The method of claim 1, the method further comprising:
   providing a filter cartridge enclosing the nanofiber filter; and
   using centrifugation to accomplish the step of separating the sperm cells of the biological sample from the digested epithelial cells.

19. The method of claim 1, the method further comprising:
   enclosing the nanofiber filter in a manifold; and
   applying within the manifold one or both of air pressure to a fluid entry side of the nanofiber filter and vacuum to a fluid exit side of the nanofiber filter during the separating step.

20. The method of claim 1, further comprised of entrapping the sperm cells in the nanofiber filter with higher than 70% efficiency.

21. A method for processing forensic samples comprised of sperm cells and non-sperm cells, the method comprising:
   selectively lysing in a lysis chamber, non-sperm cells from an epithelial cell donor of a forensic sample;
   entrapping in a nanofiber filter comprised of intermingled nanofibers having diameters of about 700 nm or less, sperm cells from the forensic sample as a first lysate is passed from the lysis chamber onto the nanofiber filter;

collecting filtered first lysate passing through the nanofiber filter;

allowing contact between sperm cells entrapped in the filter and a sperm lysing agent applied to the entrapped sperm cells to form a second lysate; and collecting the second lysate.

22. The method of claim 21, comprised of the nanofiber filter being formed as a micro fabricated device, the nanofiber filter being oriented in-line with the lysis chamber and a collection vessel disposed to collect filtered first lysate passing through the nanofiber filter.

23. The method of claim 22, comprised of the apparatus enabling generation of DNA profiles for both DNA of the sperm cells and the DNA of non-sperm cells in the sample.

24. The method of claim 21, comprised of subjecting the first lysate to a higher than ambient pressure or a lower than ambient vacuum during passage of the first lysate through the nanofiber filter.

25. The method of claim 21, comprised of selectively lysing non-sperm cells with a combination of a detergent and proteinase enzyme.

26. The method of claim 21, comprised of the sperm lysing agent comprising a mixture of a detergent, proteinase enzyme and a chemical reducing agent.

27. The method of claim 26, comprised of the chemical reducing agent comprising one of dithiothreitol (DTT) and β-mercaptoethanol.

28. The method of claim 21, comprised of isolating DNA of sperm cell and DNA of non-sperm cell from the sample.

29. A method of processing biologic samples enabling identification of human beings, the method comprised of:

selectively digesting epithelial cells from the biologic samples by using an epithelial cell digesting agent to form a digest mixture, the digest mixture including an E-fraction of digested epithelial cell DNA; and passing the digest mixture through a nanofiber filter disposed to entrap sperm cells and separate sperm cells and sperm cell DNA from non-sperm cells and non-sperm cell DNA.

30. A method of processing forensic samples, the method comprising:

applying a digesting buffer to a biological sample comprising at least sperm cells from a sperm donor and epithelial cells from an epithelial cell donor, the digesting buffer comprising a buffer material maintaining a solution pH in a physiological range, a chelating agent, a surfactant and a cell digesting enzyme to aid in digestion of epithelial cells and other non-sperm cells in the sample;

separating sperm cells of the sample from the digested epithelial cells and other non-sperm cells by filtration through a nanofiber filter comprising intermingled nanofibers disposed to entrap the sperm cells;

applying a chemical reducing agent to attain lysing of the entrapped sperm cells to provide sperm DNA;

maintaining solution pH in a physiological range by applying an eluting buffer solution comprising a buffer material, the eluting buffer comprising an eluting solvent providing purified sperm DNA; and quantitating the purified sperm DNA.

31. The method of claim 30, further comprised of:

the digesting buffer comprising tris(hydroxymethyl)aminomethane ("tris"), ethylenediamine tetraacetic acid (EDTA), sodium dodecyl sulfate (SDS) and proteinase K, the eluting buffer solution comprising tris and EDTA (TE buffer), and the cell digesting enzyme solution comprising proteinase K.

32. The method according to claim 30, further comprised of the chemical reducing agent being selected from the group consisting of dithiothreitol (DTT), β-mercaptoethanol (BME), glutathione (GSH) and combinations thereof.

33. The method according to claim 30, further comprised of separating sperm cells and sperm cell DNA from the non-sperm cells and non-sperm cell DNA in a biologic sample.

* * * * *